United States Patent [19]

Bischof et al.

[11] Patent Number: 5,516,935

[45] Date of Patent: May 14, 1996

[54] PROCESS FOR THE PRODUCTION OF DIISOCYANATES

[75] Inventors: Eric Bischof, Leichlingen; Peter Briedenbach, Rösrath; Jürgen Dahmer, Cologne; Andreas Flink, Dormagen; Attila Molnar, Odenthal; Herbert Stutz, Dormagen, all of Germany

[73] Assignee: Bayer Aktiengesellschaft, Leverkusen, Germany

[21] Appl. No.: 413,646

[22] Filed: Mar. 30, 1995

[30] Foreign Application Priority Data

Apr. 11, 1994 [DE] Germany .......................... 44 12 327.2

[51] Int. Cl.$^6$ .................................................. C07C 263/00
[52] U.S. Cl. ............................................................. 560/347
[58] Field of Search ............................................. 560/347

[56] References Cited

U.S. PATENT DOCUMENTS

| | | | |
|---|---|---|---|
| 3,631,092 | 12/1971 | Kan et al. ........................ | 260/453 PH |
| 3,651,118 | 3/1972 | Cenker et al. .................... | 260/453 PH |
| 4,419,295 | 12/1983 | Hennig et al. .................... | 260/453 PH |
| 4,847,408 | 7/1989 | Frosch et al. ..................... | 560/347 |

FOREIGN PATENT DOCUMENTS 2096501 11/1993 Canada.
1173890 12/1969 United Kingdom.

OTHER PUBLICATIONS

E. I. Dupont & Co., Res. Discl., 335, p. 195, Mar. 1992.

*Primary Examiner*—José G. Dees
*Assistant Examiner*—Samuel Barts
*Attorney, Agent, or Firm*—Joseph C. Gil; Lyndanne M. Whalen

[57] ABSTRACT

Diisocyanates are produced by gas-phase phosgenation of aliphatic diamines having two primary amino groups in the 1,2- or 1,3-position to one another or by cycloaliphatic diamines having two primary amino groups in the 1,2- or 1,3-position to one another.

6 Claims, No Drawings

1

PROCESS FOR THE PRODUCTION OF DIISOCYANATES

BACKGROUND OF THE INVENTION

The present invention relates to a process for the production of (cyclo)aliphatic diisocyanates having isocyanate groups in the 1,2-position or the 1,3-position to one another.

Preparation of organic isocyanates by reacting amines with phosgene in the gas phase is known. (See, for example, Siefken, Justus Liebigs Ann. Chem. 562, 108 (1949)). However, such processes have, until now, been recommended only for the preparation of monoisocyanates (Ullmann, 4th Edition, Volume 13, page 353), commercially available (cyclo)aliphatic diisocyanates (EP-A 0,289,840) or large-scale production of aromatic diisocyanates (DE-OS 4,217, 019 or EP-A-0593334).

(Cyclo)aliphatic 1,2- and 1,3-diisocyanates are frequently mentioned in the literature. However, these diisocyanates are not available in commercial quantities. These diisocyanates can not be produced by the classical phosgenation of the corresponding diamines in the liquid phase in high enough yields to justify their commercial production. In addition to the low yields of the raw product, the high loss of product during the working-up process (in some cases, only 30% of the isocyanate formed originally is recovered) has discouraged commercial production of these diisocyanates.

Conventional phosgenation of 1,3-diaminopentane in the liquid phase results in raw product yields of about 30% and yields of isolated product of about 10%. (E.I. DuPont and Co., Res. Discl., 335, 195 dated 1992 and work by the writer). Other disadvantages of the conventional liquid phase phosgenation process are the lengthy hot phosgenation times and the large excesses of phosgene required.

Phosgenation of 2,4(6)-diamino-1-methylcyclohexane in the liquid phase generally produces unsatisfactory yields of the corresponding diisocyanate. However, yields of up to 89% and of 92% are disclosed in German Offenlegungsschrift 2,005,309 and in Belgian Patent 745,440. These yields are reduced, however, during working-up of the raw products.

SUMMARY OF THE INVENTION

It is an object of the present invention to provide a process for the production of aliphatic and cycloaliphatic diisocyanates in which the isocyanate groups are in the 1,2- or 1,3-positions.

It is another object of the present invention to provide a process for the production of aliphatic and cycloaliphatic diisocyanates in which the isocyanate groups are in the 1,2- or 1,3-positions in yields which are significantly higher than those obtained by conventional phosgenation processes.

It is a further object of the present invention to provide a process for the production of aliphatic and cycloaliphatic diisocyanates in which the isocyanate groups are in the 1,2- or 1,3-positions which is conducted in the vapor phase.

It is also an object of the present invention to provide a process for the production of aliphatic and cycloaliphatic diisocyanates in which the isocyanate groups are in the 1,2- or 1,3-positions which does not require the lengthy phosgenation times and large excesses of phosgene of conventional processes.

These and other objects which will be apparent to those skilled in the art are accomplished by: (1) separately heating the diamine and phosgene to a temperature of from about 200° to about 600° C.; (2) introducing the heated phosgene and diamine to a cylindrical reaction chamber with no moving pads which is maintained at a temperature of from about 200° to about 600° C. in a manner such that turbulent flow is maintained while the phosgene and diamine are reacting; (3) cooling the gaseous mixture leaving the reaction chamber with an inert liquid solvent; (4) recovering a solution of diisocyanate plus inert liquid solvent; and (5) distilling the solution (4) to isolate the product isocyanate. The diamine used in this process must be selected from aliphatic diamines having two primary amino groups in the 1,2- or 1,3-positions and cycloaliphatic diamines having two primary amino groups in the 1,2- or 1,3-positions.

DETAILED DESCRIPTION OF THE INVENTION (Cyclo)aliphatic diisocyanates in which the isocyanate groups are located at the 1,2- or 1,3-positions are successfully prepared in significantly increased yields by phosgenation of the corresponding diamines when the phosgenation of the diamines and the subsequent working-up of the reaction mixture are carried out in a manner similar to that described in EP-A 0,289,840. Such improvement in yield could not have been expected by one skilled in the art. More particularly, the poor yields obtained in prior art processes are attributable to secondary reactions such as the formation of cyclic urea derivatives during the phosgenation reaction. It could not have been predicted that such secondary reactions do not occur to the same extent in the gas-phase phosgenation.

The present invention provides a process for the production of a diisocyanate by phosgenating the corresponding diamine in the gas phase, in which a) the vaporous diamine(s), optionally diluted with an inert gas or with the vapors of an inert solvent, and phosgene are heated separately to temperatures of from 200° C. to 600° C. and are caused to react continuously with one another in a cylindrical reaction chamber heated to 200° C. to 600° C., which chamber lacks moving parts, in a manner such that a turbulent flow is maintained in the reaction chamber;

b) the gas mixture continuously leaving the reaction chamber is cooled by means of an inert, liquid solvent, which is maintained at a temperature above the decomposition temperature of the carbamic acid chloride corresponding to the diamine and a solution of the diisocyanate in the inert solvent is obtained and c) the diisocyanate present dissolved in the inert solvent is subjected to working-up by distillation.

The diamine(s) used is selected from (i) aliphatic diamines having two primary amino groups in the 1,2-position or the 1,3-position to one another and (ii) cycloaliphatic diamines having two primary amino groups in the 1,2-position or the 1,3-position to one another.

The process of the present invention is suitable for the phosgenation of any aliphatic diamine having primary amino groups in the 1,2-position or 1,3-position and/or for the phosgenation of any cycloaliphatic diamine having primary amino groups in the 1,2-position or 1,3-position, provided that the diamine is stable and gaseous below the temperature conditions used in the process.

Examples of diamines useful as starting materials for the process of the present invention are diprimary aliphatic diamines having from 2 to 11 (preferably from 2 to 6) carbon atoms and two primary amino groups in the 1,2-position or the 1,3-position, and diprimary cycloaliphatic diamines having from 6 to 15 (preferably from 6 to 12) carbon atoms and two amino groups in the 1,2-position or the 1,3-position.

Preferred diamines include: 1,2-diaminoethane; 1,3-diaminopentane; 2,3-, 2,4- and 2,6-diamino-1-methylcyclohexane and mixtures of at least two of the three last-named diamines; 1,2-diaminocyclohexane; 1-methyl-3,5-diethyl-2,4-diaminocyclohexane, 1-methyl-3,5-diethyl-2,6-diaminocyclohexane and mixtures of these two last-named diamines; 1,3,5-triisopropyl-2,4-diaminocyclohexane; 2,4-diamino-1-isopropylcyclohexane; 2,6-diamino-1-isopropylcyclohexane and mixtures of the two last-named diamines.

The starting diamine is vaporized prior to use in the process of the present invention and is heated continuously to a temperature within the temperature range of from about 200° to 600° C., preferably from about 300° C. to 500° C. The heated diamine vapor can be used as such, or it may be diluted with inert gas or with the vapor of an inert solvent. Thorough mixing of the diamine vapor with the inert gas can be carried out, for example, by vaporizing the diamine in the stream of inert gas or vapor of an inert solvent. The preferred inert gas is nitrogen.

Examples of suitable inert solvents, the vapors of which may also be used to dilute the diamine, are: chlorobenzene, o-dichlorobenzene, xylene, chloronaphthalene, decahydronaphthalene and mixtures thereof.

The quantity of inert gas or solvent vapor which may optionally be used as diluent is not critical.

The phosgene is used in a stoichiometric excess (with respect to the diamine) in the process of the present invention. A quantity of phosgene corresponding to 150 to 300% of the theoretically required quantity is generally sufficient.

Prior to carrying out the process of the present invention, the stream of phosgene is heated to a temperature of from about 200° to about 600° C., preferably from about 300° to about 500° C.

To carry out the reaction in accordance with the present invention, the preheated stream of diamine or diamine-inert gas mixture on one side and the preheated stream of phosgene on the other are fed continuously into a cylindrical reaction chamber where they are mixed with one another.

Suitable cylindrical reaction chambers include tubular reactors which have no baffles or moving parts within the reactor. The tubular reactors are generally made of steel, glass, alloyed steel or glass-lined steel and are of a length which is adequate to permit a complete reaction of the diamine with the phosgene under the operating conditions. The gas streams are generally introduced into the tubular reactor at one end. These streams may be introduced, for example, via nozzles attached at one end of the tubular reactor or via a combination of a nozzle and an annular passage between the nozzle and the mixing tube.

The mixing tube is maintained at a temperature within the range of from about 200° to about 600° C., preferably from about 300° to about 500° C. This temperature may optionally be maintained by heating the tubular reactor.

It is important for the performance of the process of the present invention that the dimensions of the tubular reactor and the flow rates in the reaction chamber be calculated so that there is a turbulent flow in the reaction chamber. As used herein, "turbulent flow" means a Reynolds number of at least 2500, preferably of at least 4700. In general, this turbulence is ensured in the reaction chamber when the gaseous reactants pass through the reaction chamber at a flow rate of more than 90 m/s. The flow rate can be secured by establishing an appropriate differential pressure between the feed of the products to the reaction chamber on one side and the exit from the reaction chamber on the other. In general, the pressure in the feed lines to the reaction chamber is between about 200 and about 3000 mbar and at the exit from the reaction chamber is between about 150 and 2000 mbar. However, it is the maintenance of a pressure differential for the purpose of ensuring the above-mentioned flow rate rather than any specific pressure in the feed lines and at the exit which is important to the practice of the present invention.

After phosgenation in the reaction chamber, the gaseous mixture continuously leaving the reaction chamber is freed from the diisocyanate formed. This can be achieved, for example, by means of an inert solvent. The temperature of the inert solvent is selected so that (1) it is above the decomposition temperature of the carbamic acid chloride corresponding to the diisocyanate, and (2) the diisocyanate and the solvent (optionally employed in the vapor state as a diluent) are condensed or dissolved in the solvent while excess phosgene, hydrogen chloride and any optional inert gas (diluent) pass in gaseous form through the condensation stage or the solvent.

Solvents of the type described above as examples of suitable diluents for the diamine, particularly, technical dichlorobenzene, maintained at a temperature of from about 120° to about 200° C. (preferably from about 120° to about 170° C.) are particularly suitable for the selective recovery of the product diisocyanate from the gaseous mixture leaving the reaction chamber. Possible methods for the selective condensation of the product diisocyanate from the mixture of gases leaving the reactor using solvents of this kind include, for example, passing the gas mixture through the solvent or introducing the solvent through a nozzle (solvent cloud) into the gas stream.

After the gas mixture has been passed through the solvent to condense and recover the diisocyanate, the remaining gaseous mixture is then freed from excess phosgene in accordance with known techniques. The excess phosgene may be recovered by means of a cold trap, absorption in an inert solvent (for example, chlorobenzene or dichlorobenzene) maintained at a temperature of −10° C. to 8° C., or by adsorption and hydrolysis on activated carbon. The hydrogen chloride gas passing through the phosgene recovery stage can be recycled in accordance with known techniques to recover the chlorine required for the synthesis of phosgene.

The product diisocyanate is isolated by distillation of the solution of the diisocyanate in the inert solvent used to condense the diisocyanate.

Having thus described our invention, the following Examples are given as being illustrative thereof. All percentages given in these Examples are percentages by weight. All flow rates mentioned in the examples provide turbulent flow (Reynolds numbers of at least 2500) in the reaction chamber.

EXAMPLES

Example 1

A mixer tube heated to 400° C. having a diameter of 2.5 mm and a length of 17.5 mm to which a diisocyanate condensation stage was connected in tandem was used in this Example. The condensation stage was connected to a phosgene adsorption tower filled with activated carbon. Phosgene which was preheated to a temperature of 420° C.

was passed continuously at a rate of 5.9 mol/hour through a nozzle which projected into the mixer tube. The phosgene was preheated to a temperature of 420° C. at a pressure of 950 mbar in a heat exchanger connected in series. At the same time, a mixture of 1,3-diaminopentane and nitrogen (diluent) heated to 250° C. was fed into the mixer tube at a rate of 1 mol/hour of 1,3-diaminopentane and 0.1 mol/hour of nitrogen through an annular passage between the nozzle and the mixer tube. A pressure of approximately 350 mbar was maintained in the mixer tube by applying a vacuum at the end of the diisocyanate condensation stage. The hot gaseous reaction mixture leaving the reaction chamber was passed through dichlorobenzene, which was maintained at a temperature of from 150° to 160° C. Here the selective condensation of the diisocyanate formed took place. The gas mixture passing through the washing stage (made up largely of nitrogen, hydrogen chloride and excess phosgene) was subsequently freed from phosgene in the adsorption tower. Pure diisocyanate was obtained by distillation from the washing solvent. The yield of pure 1,3-pentane diisocyanate was 80% of the theoretical yield.

Comparison Example (Liquid phase phosgenation of 1,3-diaminopentane):

$CO_2$ was passed into a mixture of 38 g of 1,3-diaminopentane and 1000 g of 1,2-dichlorobenzene until the saturation point was attained. The carbamate-solvent mixture thus obtained was then added dropwise over a period of approximately 1 hour to a solution of 220 g of phosgene in 100 g of 1,2-dichlorobenzene which was maintained at approximately 0° C. The reaction mixture was subsequently heated to 170° C. (boiling temperature of the solvent), while 24 l/hour of phosgene gas was passed through continuously, and maintained at this temperature for 4 hours. The reaction mixture thus obtained contained 25% of the theoretical yield of 1,3-diisocyanatopentane. After working up by distillation, the 1,3-diisocyanatopentane was obtained at 93% purity in a yield of 17% of the theoretical yield.

Example 2

The procedure of Example 1 was repeated using the same device and conditions with the exception that an isomeric mixture of 65% of 2,4-diamino-1-methylcyclohexane and 35% of 2,6-diamino-1-methylcyclohexane introduced into the tube reactor at a rate of 1 mol/hour and phosgene introduced into the tube reactor at a rate of 5.9 mol/hour of phosgene were used. Nitrogen was used as the diluent for the amine in an amount of 0.1 mol/hour. 2,4(6)-diisocyanato-1-methyl-cyclohexane was produced in a 98% yield. Working up by distillation was successfully carried out without difficulty and produced 96% of the theoretical yield of pure diisocyanate.

Example 3

The procedure of Example 1 was repeated using the same device and conditions with the exception that an isomeric mixture of 2,4(6)-diamino-3,5-diethyl-1-methylcyclohexane introduced into the tube reactor at a rate of 1 mol/hour, phosgene introduced into the tube reactor at a rate of 5.9 mol/hour of phosgene, and nitrogen as diluent for the diamine in an amount of 0.1 mol/hour were used. 3,5-diethyl-2,4-(6)-diisocyanato-1-methylcyclohexane was obtained in a 99% yield. Working up by distillation was successfully carried out without difficulty and produced 98% of the theoretical yield of pure diisocyanate.

Example 4

The procedure of Example 1 was repeated using the same device and the same conditions with the exception that a cis/trans-isomeric mixture of 1,2-diaminocyclohexane introduced into the tube reactor at a rate of 1 mol/hour, phosgene introduced into the tube reactor at a rate of 5.9 mol/hour and 0.1 mol/hour of nitrogen as diluent for the diamine were used. The 1,2-diisocyanatocyclohexane was recovered in a 52% yield. Working up by distillation was successfully carried out without difficulty and produced 42% of the theoretical yield of pure diisocyanate.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a diisocyanate comprising
   a) heating a vaporous diamine selected from
      1) aliphatic diamines having two primary amino groups in the 1,2- or 1,3-positions to one another and
      2) cycloaliphatic diamines having two primary amino groups in the 1,2- or 1,3-positions to one another to a temperature of from about 200° to about 600° C.,
   b) heating phosgene to a temperature of from about 200° to about 600° C.,
   c) introducing the diamine from step a) and the phosgene from step b) into a cylindrical reaction chamber heated to a temperature of from about 200° to about 600° C., which reaction chamber has no moving pads, in a manner such that a turbulent flow is maintained in the reaction chamber and the diamine from step a) and phosgene from step b) are reacted,
   d) cooling any gas leaving the reaction chamber by means of an inert liquid solvent that is maintained at a temperature above the decomposition temperature of carbamic acid chloride corresponding to the diamine used in step a),
   e) recovering a solution of diisocyanate plus inert liquid solvent, and
   f) distilling the solution recovered in step e) to isolate the product diisocyanate.

2. The process of claim 1 in which the diamine of step a) is diluted with an inert gas or with the vapors of an inert solvent prior to step c).

3. The process of claim 2 in which nitrogen is used as the diluent for the diamine from step a).

4. The process of claim 1 in which the diamine used in step a) is selected from the group consisting of: 1,2-diaminoethane; 1,3-diaminoethane; 2,3-diamino-1-methylcyclohexane; 2,4-diamino-1-methylcyclohexane; 2,6-diamino-1-methylcyclohexane; mixtures of 2,3-diamino-1-methylcyclohexane and 2,4-diamino-1-methylcyclohexane; mixtures of 2,3-diamino-1-methylcyclohexane and 2,6-diamino-1-methylcyclohexane; mixtures of 2,4-diamino-1-methylcyclohexane and 2,6 -diamino-1-methylcyclohexane; mixtures of 2,3-diamino-1-methylcyclohexane, 2,4-diamino-1-methylcyclohexane and 2,6-diamino-1-methylcyclohexane; 1,2-diaminocyclohexane; 1-methyl-3,5-diethyl-2,4-diaminocyclohexane; 1-methyl-3,5-diethyl-2,6-diaminocyclohexane; mixtures of 1-methyl-3,5-diethyl-2,4-diaminocyclohexane and 1-methyl-3,5-diethyl-2,6diaminocyclohexane; 1,3,5-triisopropyl-2,4- diaminocyclohexane; 2,4-diamino-1-isopropylcyclohexane; 2,6-diamino-1-isopropyl-cyclohexane; and mixtures of 2,4-diamino-1-isopropylcyclohexane and 2,6-diamino-1-isopropylcyclohexane.

5. The process of claim 1 in which the turbulent flow prevailing in the reaction chamber during step c) corresponds to a Reynolds number of at least 2500.

6. The process of claim 1 in which step c) is carried out in a reaction chamber maintained at a temperature of from about 300° to about 500° C.

* * * * *